(12) United States Patent
Ye

(10) Patent No.: US 7,546,653 B2
(45) Date of Patent: Jun. 16, 2009

(54) AIR MATTRESS

(76) Inventor: Yongfeng Ye, No. 34, East Hengyang Road, Kunyang Town, Pingyang County, Wenzhou, Zhejiang, 325400 (CN)

( * ) Notice: Subject to any disclaimer, the term of this patent is extended or adjusted under 35 U.S.C. 154(b) by 560 days.

(21) Appl. No.: 11/210,509

(22) Filed: Aug. 23, 2005

(65) Prior Publication Data

US 2006/0053558 A1    Mar. 16, 2006

(30) Foreign Application Priority Data

Aug. 27, 2004 (CN) ............... 2004 1 0540805
Jan. 19, 2005 (CN) ............... 2005 1 0006510

(51) Int. Cl.
*A61G 7/057* (2006.01)
(52) U.S. Cl. ............... 5/689; 5/636; 5/421; 5/715; 601/15; 601/16; 601/49; 607/104
(58) Field of Classification Search ............... 5/421, 5/693, 704, 706, 710, 713, 724, 906, 915, 5/933, 636, 689, 715; 607/104; 601/15, 601/16, 49
See application file for complete search history.

(56) References Cited

U.S. PATENT DOCUMENTS

| | | | | |
|---|---|---|---|---|
| 3,085,568 A | * | 4/1963 | Whitesell | 601/55 |
| 3,854,474 A | * | 12/1974 | Carruth | 601/49 |
| 4,066,072 A | * | 1/1978 | Cummins | 601/15 |
| 4,330,892 A | * | 5/1982 | Fukushima | 5/636 |
| 4,680,822 A | * | 7/1987 | Fujino et al. | 5/421 |
| 5,437,608 A | * | 8/1995 | Cutler | 601/49 |
| 5,462,515 A | * | 10/1995 | Tseng | 601/57 |
| 5,564,142 A | * | 10/1996 | Liu | 5/689 |
| 5,966,763 A | * | 10/1999 | Thomas et al. | 5/715 |
| 6,212,719 B1 | * | 4/2001 | Thomas et al. | 5/713 |
| 6,529,533 B1 | * | 3/2003 | Voss | 372/29.01 |
| 6,606,754 B1 | * | 8/2003 | Flick | 5/421 |
| 6,695,798 B2 | * | 2/2004 | Chang | 601/49 |
| 2007/0032752 A1 | * | 2/2007 | Wu | 601/57 |

* cited by examiner

*Primary Examiner*—Roy D Gibson
*Assistant Examiner*—Kaitlyn E Helling
(74) *Attorney, Agent, or Firm*—Raymond Y. Chan; David and Raymond Patent Firm

(57) ABSTRACT

An air mattress includes a mattress envelope having a compartment and comprising a thermal functional layer and an outer layer overlapped thereon and an air cushion including a plurality of individual air chambers evenly disposed in the compartment of the mattress envelope and an air supplying tube communicatively interconnecting the air chamber with each other. A thermal control arrangement includes a liquid supplying tube spirally extending at the thermal functional layer of the mattress envelope for guiding a flow of thermal liquid and a thermal energy generator arranged to regulate a temperature of the thermal liquid such that when the thermal liquid passes through the liquid supplying tube, the thermal liquid thermo-communicating with the thermal functional layer of the mattress envelope towards the outer layer so as to regulate a temperature of the mattress envelope.

6 Claims, 16 Drawing Sheets

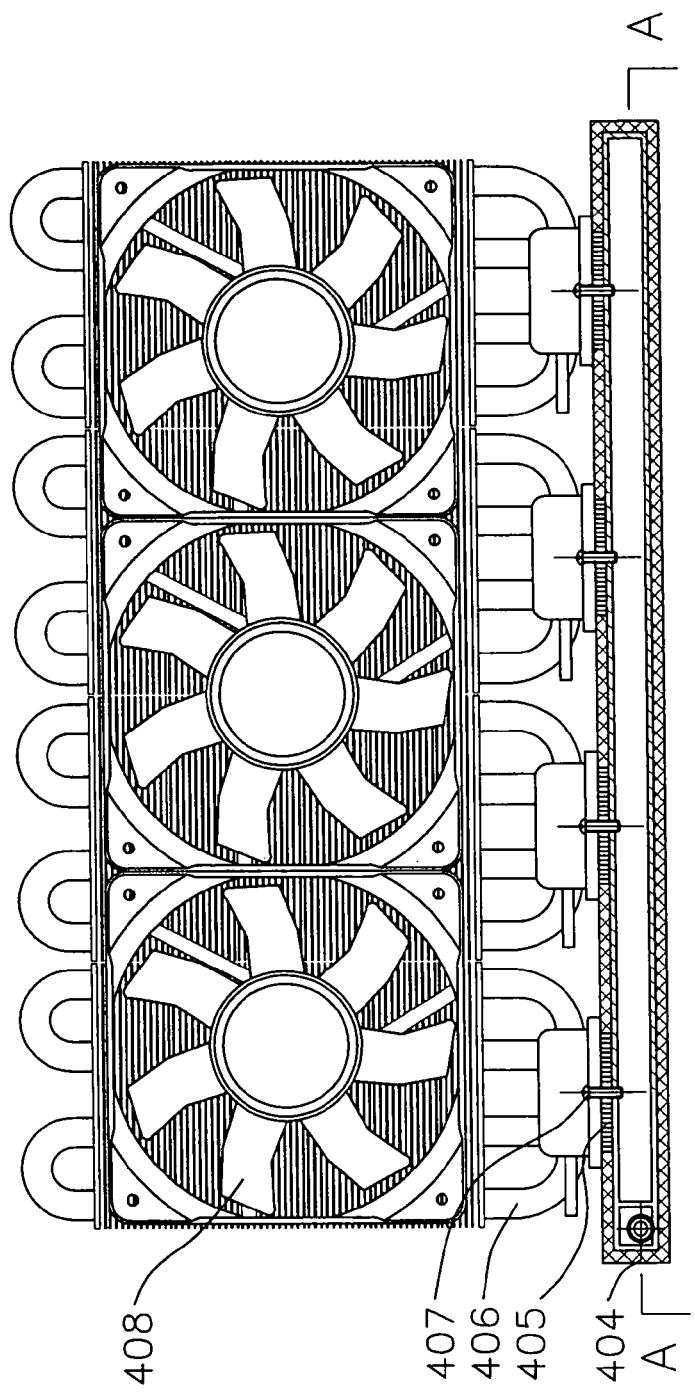
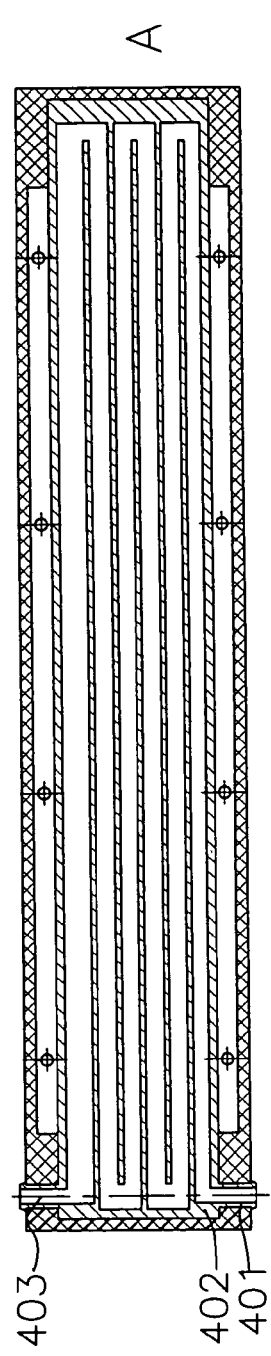
FIG.6A
FIG.6B

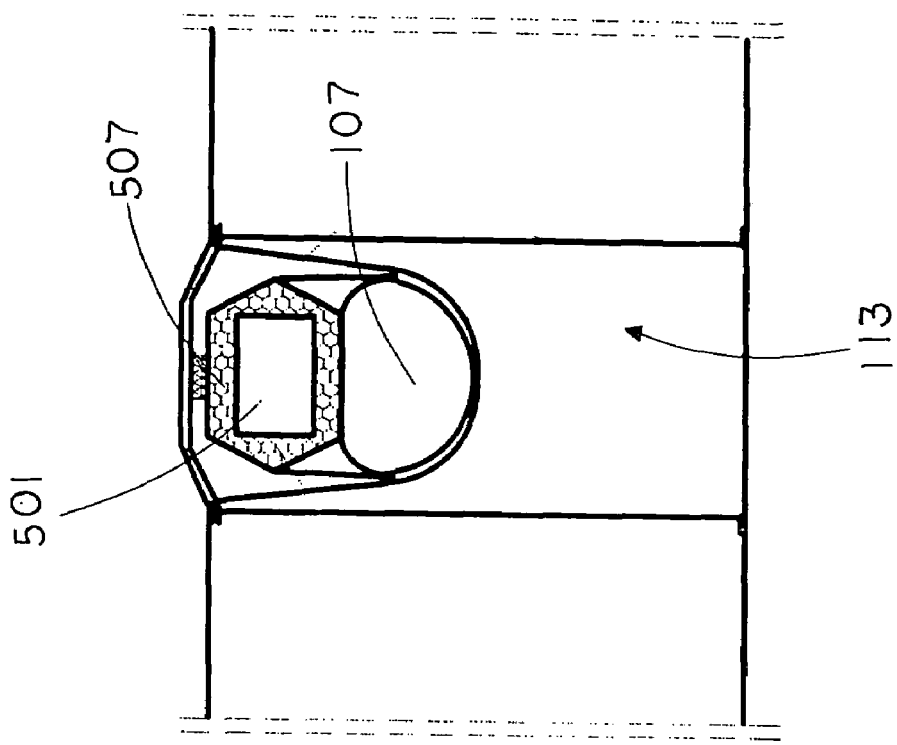
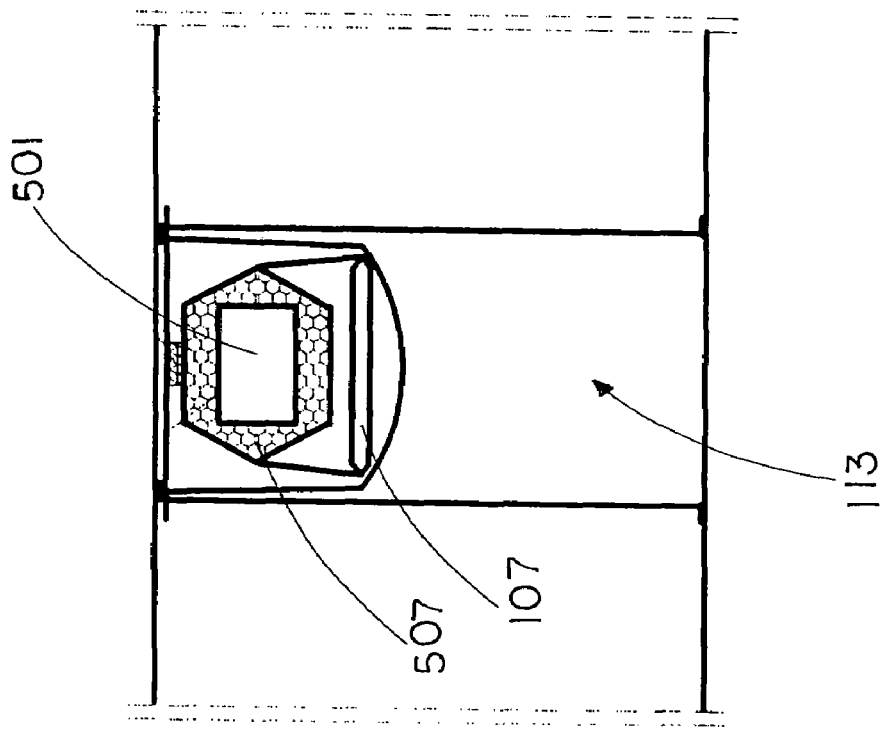
FIG 8B
FIG 8A

AIR MATTRESS

BACKGROUND OF THE PRESENT INVENTION

1. Field of Invention

The present invention relates to air mattress, and more particularly to an air mattress, which uses as a substitution for a conventional spring mattress, providing a temperature adjustable function and/or a massage function.

2. Description of Related Arts

Conventional spring mattress includes a mattress envelope and an air cushion received therein. The conventional spring mattress generally employs steel springs or sponges as supporters for the air cushion. Accordingly, such mattress is cumbersome and is inconvenient to be transported from one place to another place. Additionally, the steel springs and the sponges tend to become fatigue and aging after long time use such that the rigidity of the mattress will not be evenly distributed. Moreover, the rigidity of the conventional mattress is non-adjustable. The conventional mattress is incapable of being suitably adapted to various weights, and contours of human bodies.

SUMMARY OF THE PRESENT INVENTION

A main object of the present invention is to provide an air mattress which has individual air chambers allowing to be inflated to provide an even supporting surface to support a user thereon. In other words, the rigidity of the air mattress can be selectively adjusted by the volume of air inflated into the individual air chambers.

Another object of the present invention is to provide an air mattress having a temperature adjustable function such that the user is able to selectively adjust the temperature of the supporting surface of the mattress to provide an optimal resting condition.

Another object of the present invention is to provide an air mattress having a massage function.

In one aspect of the present invention, there is provided an air mattress. The air mattress comprises a mattress envelope and an air cushion received in the mattress envelope. The mattress envelope comprises a liquid supplying tube for guiding a thermo (cold or warm) liquid. The liquid supplying tube is arranged in a predetermined pattern. The air cushion comprises a plurality of separated air chambers and air supplying tubes. The air supplying tubes are communicatively interconnecting the air chambers to each other. The air mattress further comprises a thermo (cold or warm) energy generator and an air charger. The thermo (cold or warm) energy generator comprises an electrical heat generator which comprises a container for containing the liquid therein, an electrical heater and a pump disposed within the container. The container communicates with an outlet of the liquid supplying tube for transportation of thermo (cold or warm) liquid via a pipe. The pump is provided for transferring the liquid in the container to an inlet of the liquid supplying tube via the pipe. The air charger comprises an outlet in communication with the air supplying tube of the air cushion.

In another aspect of the present invention, the air mattress comprises a mattress envelope and an air cushion provided within the mattress envelope. The mattress envelope comprises a liquid supplying tube for guiding a thermo (cold or warm) liquid. The liquid supplying tube is arranged in a predetermined pattern. The air cushion comprises a plurality of separated air chambers and an air supplying tube. The air supplying tube interconnects the air chambers to each other. The air mattress further comprises a semiconductor thermo (cold or warm) energy generator, a container for containing the liquid, a pump provided within the container and an air charger. The semiconductor thermo (cold or warm) energy generator comprises a semiconductor thermo (cold or warm) generating plate, and a heat exchanger attached to one side of the semiconductor thermo (cold or warm) generating plate which comprises an inlet and an outlet. The pump is provided for transferring the liquid in the container to the inlet of the heat exchanger. The outlet of the heat exchanger communicates with the inlet of the liquid supplying tube. The air charger comprises an outlet in communication with the air supplying tube of the air cushion.

In still another aspect of the present invention, the air mattress comprises a mattress envelope and an air cushion provided within the mattress envelope. The air cushion comprises a plurality of separated air chambers and an air supplying tube for interconnecting the air chambers to each other. At least some of the air chambers are provided therein with massagers, air bags located beneath the massager for supporting the corresponding massagers, and air supplying tubes in communication with the corresponding air bags. The air mattress further comprises an air charger having outlet in communication with the air supplying tube of the air cushion and the air supplying tubes of the air bags.

The above and other features of the invention, including various novel details of construction and combination of parts, will now be more particularly described with reference to the accompanying drawings.

These and other objectives, features, and advantages of the present invention will become apparent from the following detailed description, the accompanying drawings, and the appended claims.

BRIEF DESCRIPTION OF THE DRAWINGS

FIG. 6A is a schematic view of the thermal energy generator of the air mattress according to the above preferred embodiment of the present invention.

FIG. 6B is a sectional view of the thermal energy generator of the air mattress according to the above preferred embodiment of the present invention.

FIG. 8A is a sectional view of the massaging arrangement of the air mattress according the above preferred embodiment of the present invention, illustrating the massaging arrangement is received within the air chamber with a stand-by manner.

FIG. 8B is a sectional view of the massaging arrangement of the air mattress according to the above preferred embodiment of the present invention, illustrating the massager bags are filled with pressurized air for upwardly urging the massager in massaging position.

DETAILED DESCRIPTION OF THE PREFERRED EMBODIMENT

Figure 1:
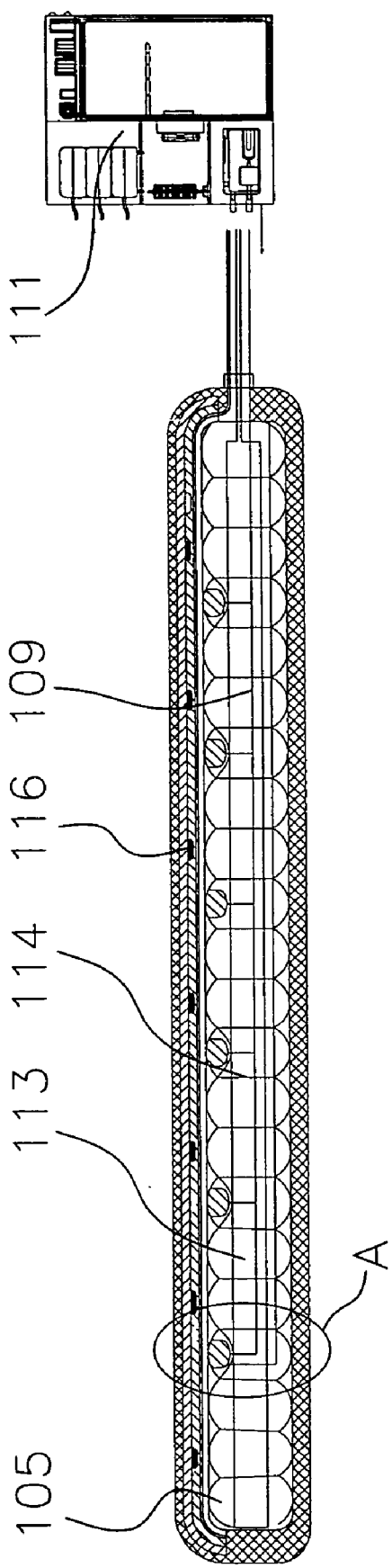
FIG. 1 is a sectional view of an air mattress and a control center according to a preferred embodiment of the present invention.

Referring to FIG. 1 of the drawings, an air mattress according to a preferred embodiment of the present invention is illustrated, wherein the air mattress comprises an air cushion 105, a mattress envelope having a compartment for enclosing the air cushion 105 therein, and a control center 111.

Figure 2:
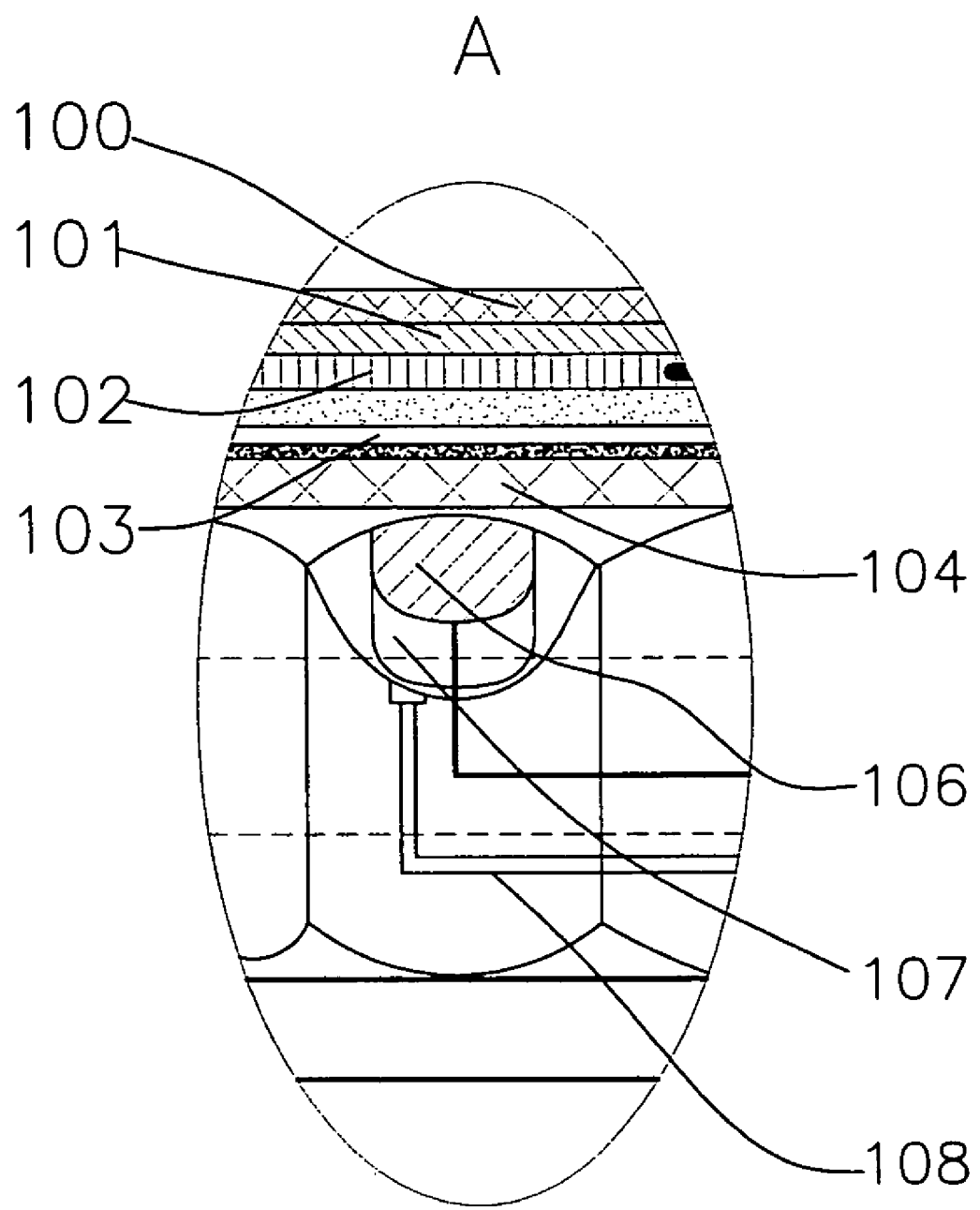
FIG. 2 is a partially sectional view of an air chamber of the air mattress according to the above preferred embodiment of the present invention.
Figure 3:
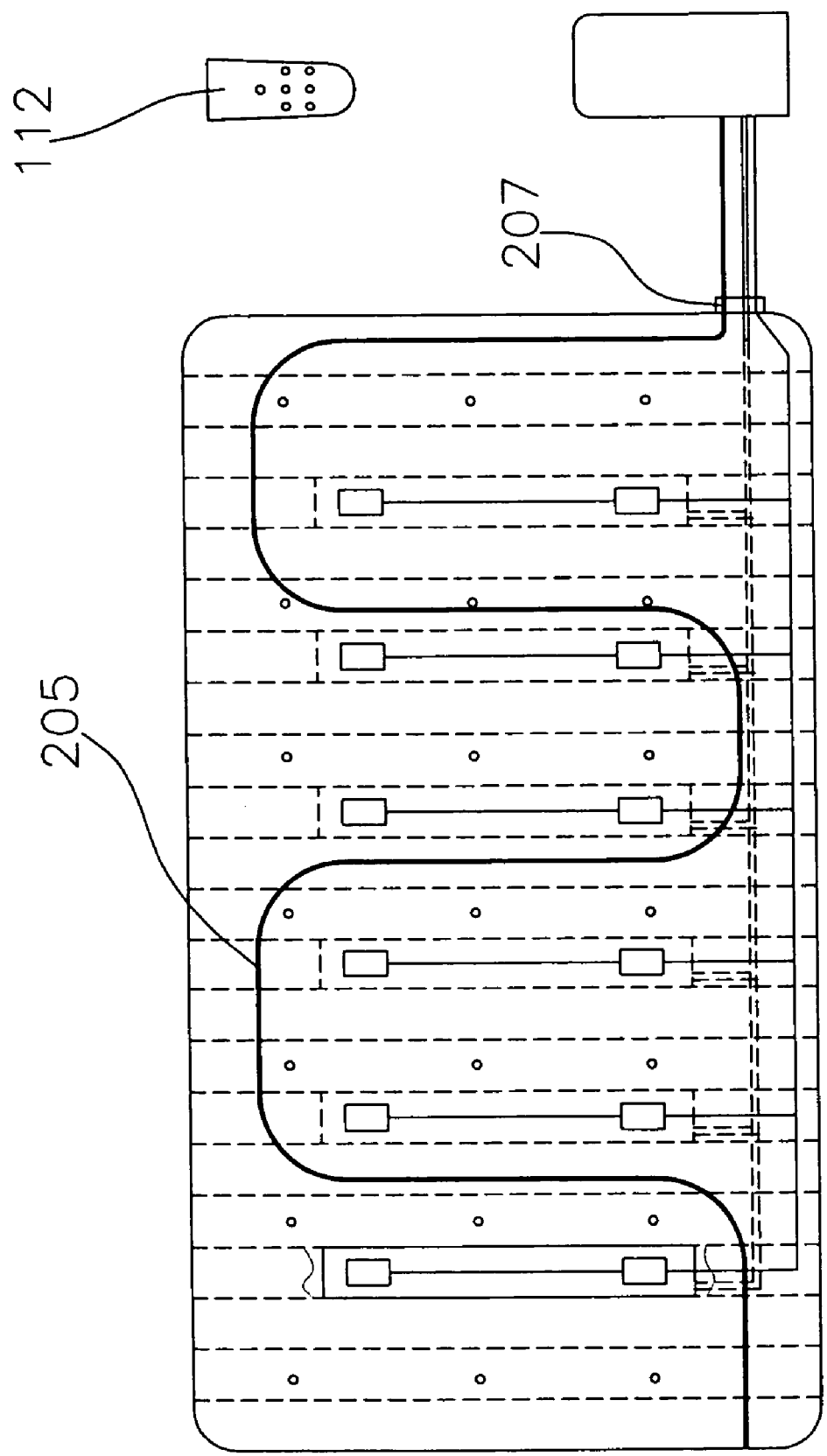
FIG. 3 is a top schematic view of the air mattress according to the above preferred embodiment of the present invention, illustrating the thermal control arrangement.
Figure 8:
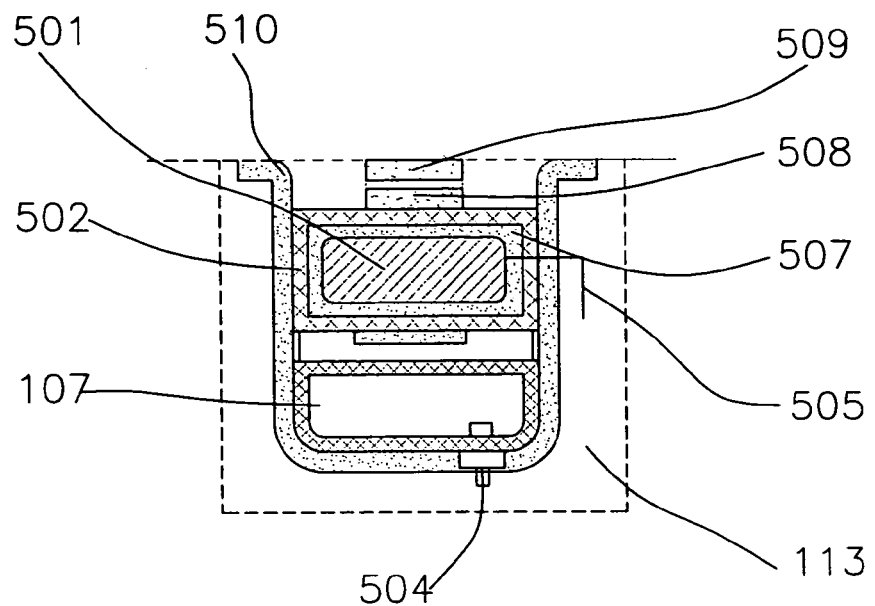
FIG. 8 is a sectional view of the massaging arrangement of the air mattress according to the above preferred embodiment of the present invention.

Referring to FIGS. 2 and 3, the air cushion 105 comprises a plurality of partition walls 114 forming a plurality of separated air chambers 113. When the air chamber 113 is filled with air, a flat surface of the air cushion 105 is formed accordingly due to restriction of the partition walls 114. Accordingly, the air cushion 105 is made of durable material, such as plastic, having a predetermined strength intensity, air-tightness, and welding capacity. A plurality of suspension bags 510, as shown in FIG. 8, is arranged respectively within some of the air chambers 113 for installation of corresponding massager devices 106 therein which will be particularly described later. A plurality of air inlets is defined respectively in the corresponding air chambers 113 for introducing the air into the air chambers 113 and air bags 107 of the massager devices 106 which will be particularly described later. Additionally, a controlling electrical wire 109 of the massager devices 106 is securely embedded within the air cushion 105.

The mattress envelope, from an exterior to an interior thereof, comprises an outer covering layer 100, a far infrared emission functional layer 101 and a magnetic functional layer 102 both for serving purposes of health care, a thermo (cold or warm) functional layer 103, and a ventilating layer 104. Preferably, the outer covering layer 100 is made of full cotton to enhance the comfortability of the mattress envelope. The far infrared emission functional layer 101 is provided for improving micro-circulation of blood capillary in a skin of a user. Fabricating techniques of the far infrared emission functional layer 101 is well known to the ordinary skilled person, and will not be illustrated hereinafter. The magnetic functional layer 102 comprises a plurality of permanent magnets 116 arranged at an interval of 20 cm. The ventilating layer 104 is provided for avoiding occurrence of humidification caused by temperature difference between the thermo (cold or warm) functional layer 103 and the air cushion 105.

Figure 4:
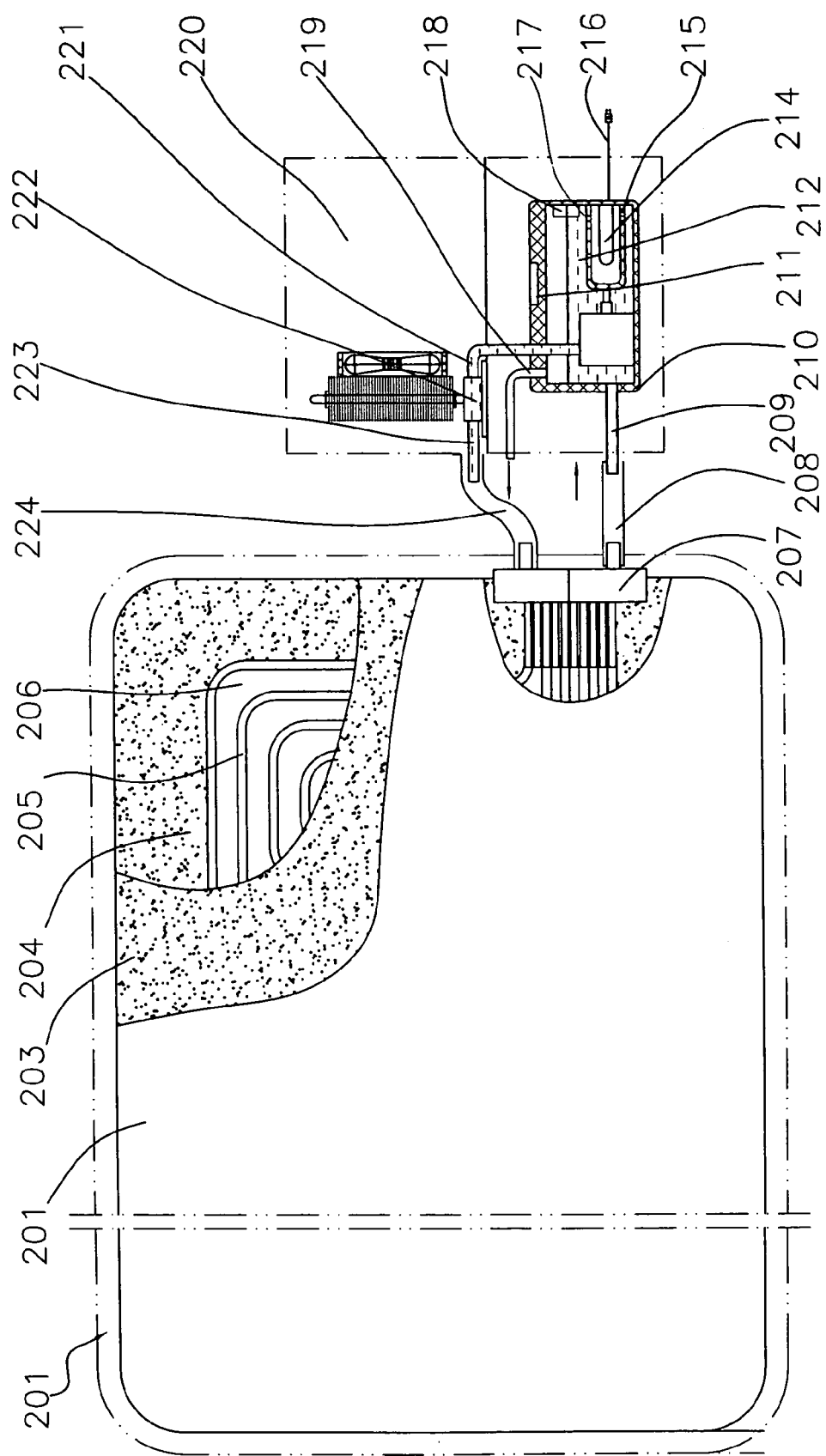
FIG. 4 is a sectional view of the thermal control arrangement of the air mattress according to the above preferred embodiment of the present invention.

Referring to FIG. 4, the thermo (cold or warm) functional layer 103 comprises a thermo (cold or warm) bedspread 201, a cloth cover 202, a heat preservation enclosure 203, a tube arranging layer 204, a positioning layer 206, and a thermo (cold or warm) supplying tube 205. The thermo (cold or warm) supplying tube 205 is embedded in the tube arranging layer 204. The thermo (cold or warm) supplying tube 205 is fixed to the positioning layer 206 and is arranged in a zigzag fashion. The thermo (cold or warm) supplying tube 205 communicates with a water distributor 207. A water supplying tube 224 and a water exhausting tube 208 are incorporated in the water distributor 207, respectively. The tube arranging layer 204 is enclosed in the heat preservation enclosure 203 which is covered with the cloth cover 202.

The air mattress further comprises a thermal control arrangement for regulating a temperature of the thermo (cold or warm) functional layer 103. The thermal control arrangement comprises a thermo (cold or warm) energy generator 220 comprising a thermal source which is embodied as an electrical heat source generator or a semiconductor thermo (cold or warm) energy generator 222.

Figure 5:
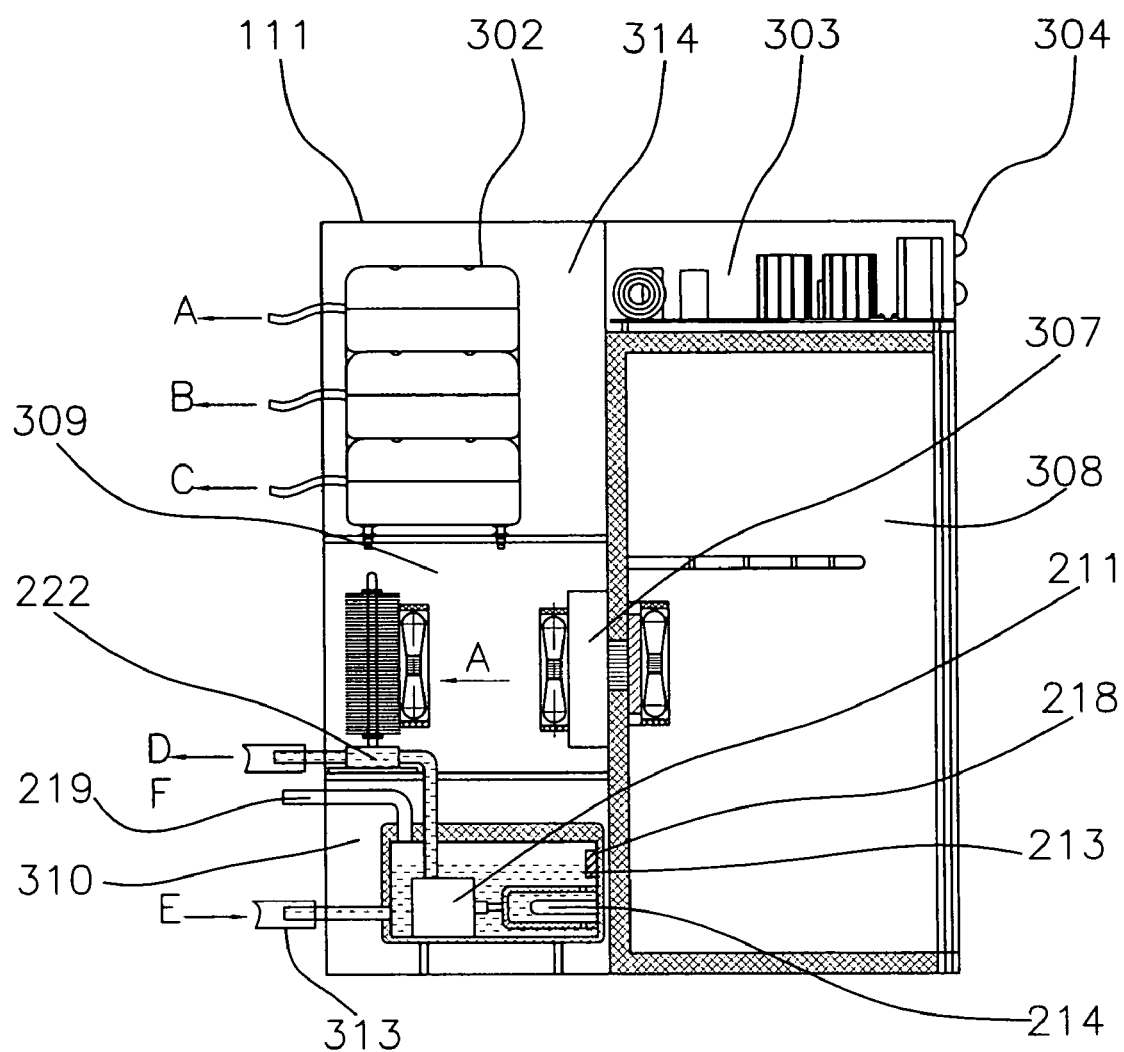
FIG. 5 is a sectional view of a thermal energy generator of the air mattress according to the above preferred embodiment of the present invention.

With reference to FIG. 5, the electrical heat source generator comprises the water tank 213, a heat preservation tube 215, an electrical heater 214 received in the heat preservation tube 215, a water pump 211, and a water level monitor 218. The electrical heater 214 is disposed in the water tank 213. An electrical wire 216 of the electrical heater 214 is disposed at an exterior of the water tank 213. A water inlet 217 is defined in the heat preservation tube 215. The heat preservation tube 215 communicates with the water pump 211. The water level monitor 218 is disposed within the water tank 213 in case of lack of water. Certain amount of water is introduced into the water tank 213 via a water supplying pipe 219. A heat preservation overcoat 210 is preferably formed on an outer surface of the water tank 213. The water pump 211 is adapted for transferring a liquid in the heat preservation tube 215 to an inlet 401 of a heat exchanger 402 (shown in FIG. 6B) via pipes. A controlling circuit 212 of the thermo (cold or warm) energy generator 220 is generally arranged on a cover portion of the water tank 213.

Referring to FIGS. 6A and 6B, the semiconductor thermo (cold or warm) energy generator 222 comprises the heat exchanger 402, a semiconductor plate 405 for generating cold or heat energy, a heat pipe heat sink 406, a low noise fan 408, and a heat preservation coating 404. The heat exchanger 402 is generally a flat plate defining a circulatory channel therethrough. The semiconductor plate 405 is controlled by a controlling circuit. The heat exchanger 402 is attached to one side of the semiconductor plate 405. An inlet 401 and an outlet 403 of the circulatory channel of the heat exchanger 402 are connected respectively to the water pump 211 and the water supplying tube 224 of the water distributor 207 via tubes 221 and 223. The heat preservation coating 404 is formed on an outer surface of the heat exchanger 402. The heat pipe heat sink 406 is attached to the other side of the semiconductor plate 405. The heat pipe heat sink 406 is secured to the heat exchanger 402 by screws 407.

The semiconductor thermo (cold or warm) energy generator 222 communicates with the electrical heat source generator via the water pump 211. The semiconductor thermo (cold or warm) energy generator 222 and the electrical heat source generator cooperatively form the thermo (cold or warm) source generator 220. Heated water or cooled water generated from the thermo (cold or warm) source generator 220 is supplied from the water pump 211 to the thermo (cold or warm) functional layer 103 via the water supplying tube 224. After heat exchange, the water in the thermo (cold or warm) supplying tube 205 flows back to the water tank 213 through an inlet opening 209 thereof via a water exhausting tube 208.

In other words, the container (water tank 213) is communicating with the water supplying tube 205 in a circulating manner wherein the pump 211 is arranged to pump the thermal liquid from the container to the water supplying tube 205 through the heat exchanger 402 such that the thermal liquid is guided to flow at the thermal functional layer 103 of the mattress envelope and back to the container.

In the present embodiment, the water as the thermal liquid can be heated by means of the semiconductor plate 405 or the electrical heater 214.

1. Water heated by the semiconductor plate: when the semiconductor thermo (cold or warm) energy generator 222 is powered on, the heat exchanger 402 is heated up accordingly, due to heat exchange between the semiconductor plate 405 and the heat exchanger 402. The water in the water tank 213 is transferred to the circulatory channel of the heat exchanger 402 by the water pump 211, and is then heated up by the heat exchanger 402.

2. Water heated by the electrical heater: in this mode, the water in the water tank 213 is heated by the electrical heater 214.

In the present embodiment, the water is cooled by means of the semiconductor plate 405.

When the semiconductor thermo (cold or warm) energy generator 222 is powered on, the semiconductor plate is cooled down. The heat exchanger 402 is also cooled down due to the heat exchange. The water in the water tank 213 is transferred to the circulatory channel of the heat exchanger 402 by the water pump 211, and is then cooled down by the heat exchanger 402, accordingly. The cooled water is then supplied to the thermo (cold or warm) supplying tube 205 by the water pump 211.

In other words, the semiconductor plate is arranged to generate a thermal energy wherein the heat exchanger 402 is coupled with the semiconductor plate for heat-transferring the thermal energy to the thermal liquid such that the thermal liquid is adapted to be selectively refrigerated and heated up by the semiconductor plate through the liquid supplying tube 224 for refrigerating and warming the mattress envelope respectively.

Figure 7:
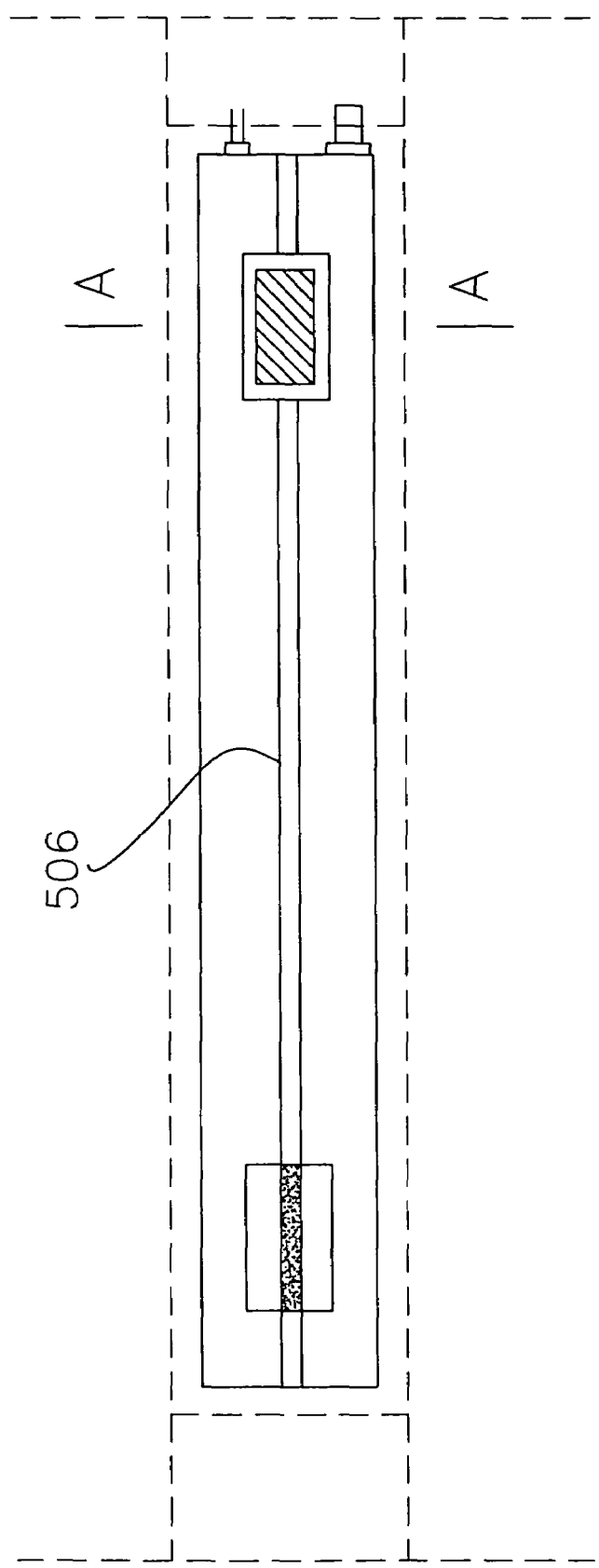
FIG. 7 is a schematic view of a massaging arrangement of the air mattress according to the above preferred embodiment of the present invention.

Referring to FIGS. 7 and 8, in order to achieve the massage function of the air mattress, the air mattress further comprises a plurality of massagers 501, massager bags 502 containing the massagers 501 therein, buffer materials 507 received in the massager bags 502, the air bags 107 for supporting the massagers 501, an air inlet tube 504 for introducing air therethrough, power wires 505 of the massagers 501, the suspension bags 510 accommodating the massager bags 502 and the air bags 107 therein, draught bands 506, lower fixing glue patches 508 affixed to the massager bags 502, and upper fixing glue patches 509 formed on top portions of the air chambers 113. In other words, the respective massager 501 is suspendedly supported in the air chamber 113 at a position that the massager 501 is mounted underneath the outer layer 100 of the mattress envelope so as to transfer the massaging force towards the outer layer 100 of the mattress envelope as shown in FIG. 8A and FIG. 8B.

As aforementioned, upon effect of the partition walls 114, the air chambers 113 are formed in the air mattress. The suspension bags 510 are attached in the corresponding air chambers 113. The air bags 107 are disposed in the suspension bags 510 and connected with each other by the draught bands 506, as shown in FIG. 7. The massager bags 502 are firmly positioned within the suspension bags 510 by affixing the upper fixing glue patches 509 to the lower fixing glue patches 508.

Figure 10:
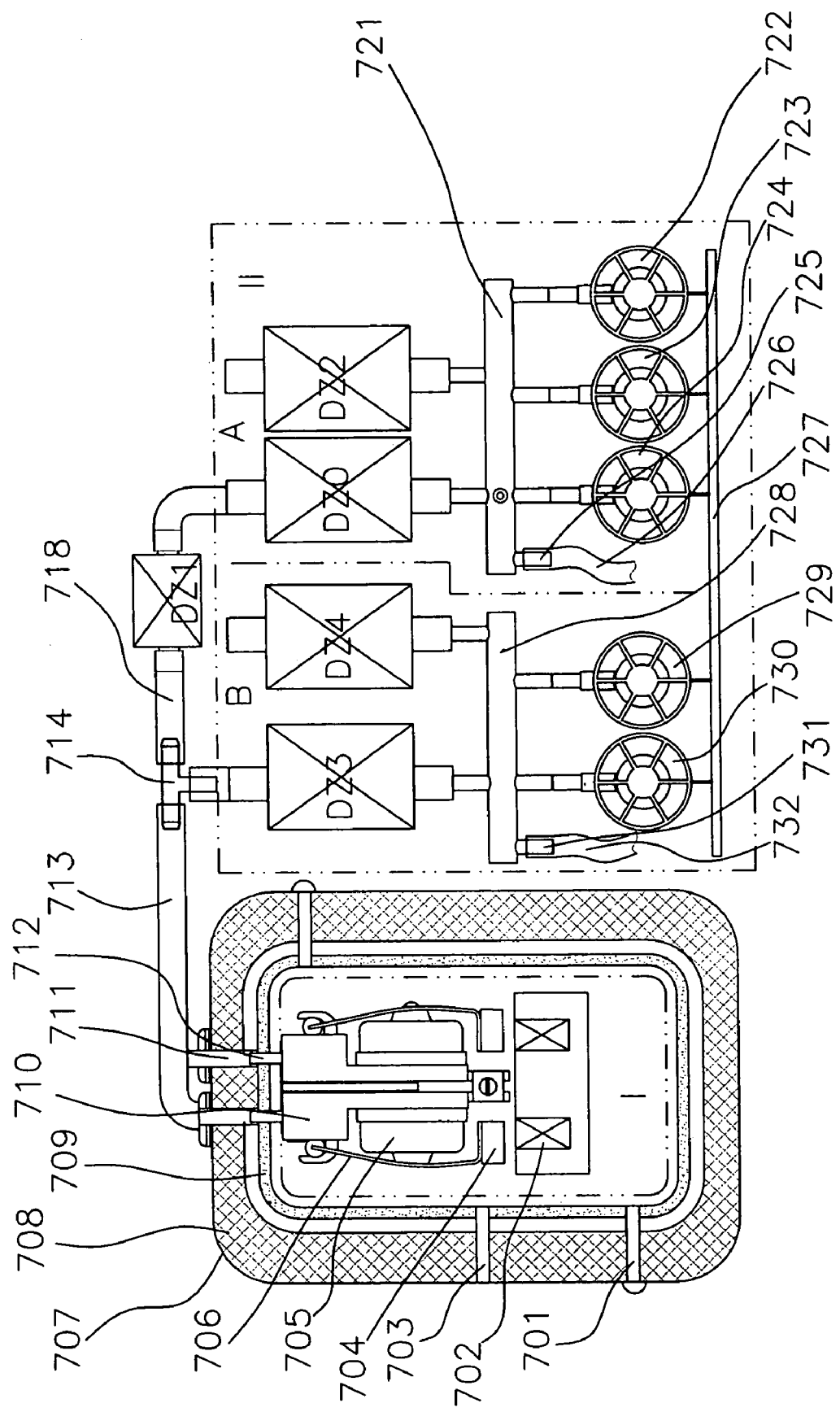
FIG. 10 is a schematic view of an air charger of the air mattress according to the above preferred embodiment of the present invention.

The air bags 107 are located beneath the massager bags 502. The air bags 107 are connected with air charging pipes 108 as shown in FIG. 2. The air charging pipe 108 is connected with the air inlet tube 504 and in communication with an air outlet 712, as shown in FIG. 10, of the air generator via.

Figure 9:
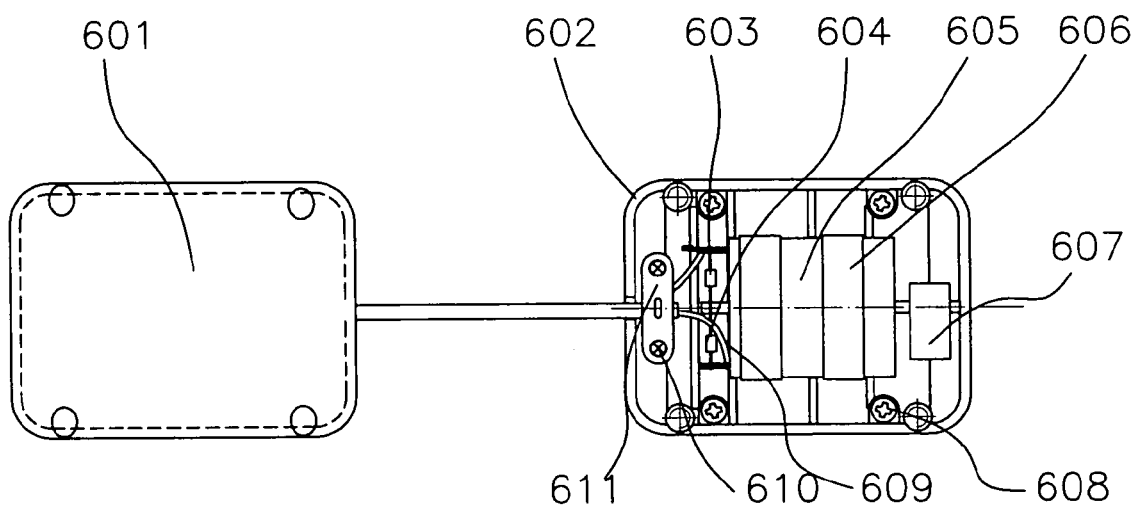
FIG. 9 is a sectional view of the massaging unit according to the above preferred embodiment of the present invention.

Referring to FIG. 9, the massager 501 is driven by an eccentric wheel motor. The massager 501 comprises a top cover 601, a bottom cover 602, an over-current protector 603, an arc preventing protector 604, a massager motor 605, an anti-vibration protection gasket 606 for massager motor 605, an eccentric wheel 607, fixing screws 608, an electrical wire 609, a fastener 610 for fastening the electrical wire 609, and a wire clamp 611. The structure and the operational principle of the massager 501 are well known to the ordinary skilled person, and will not be illustrated in detail hereinafter.

The massager 501 is electrically connected to an integrated circuit IC1 (shown in FIG. 11) via the power wire 505.

An operational principle of the massager 501 is explained as follows: when the air cushion 105 is filled with compressed air at a certain pressure, the massagers 501 are suspended by the suspension bags 510. The massagers 501 are securely attached to the suspension bags 510 by affixing the upper and lower glue patches 509, 508 to each other. In this state, the air mattress is operated in a normal state, and the user laid on the air mattress cannot feel existence of the massage devices 106. When the massage function is activated, the air bags 107 are further charged by the air generator such that the air pressure of the air bags 107 reaches a predetermined pressure value. The air bags 107 are then forced to support the massagers 501 upwardly. Meanwhile, the massagers 501 start to operate upon execution of a massage instruction. In other words, when the air bag 107 is pumped in an inflated manner, the respective massager 501 is pushed upward while each of the massagers 501 generates a massaging force towards the outer layer 100 of the mattress envelope.

During the massage process, the air pressure of the air bags 107 is kept constantly. When the massagers 501 are turned off, an air exhausting electromagnetic valve DZ4 for the air bags 107 (shown in FIG. 10) is opened to exhaust the air such that the air mattress is resumed to operate in the original normal state.

Figure 11:
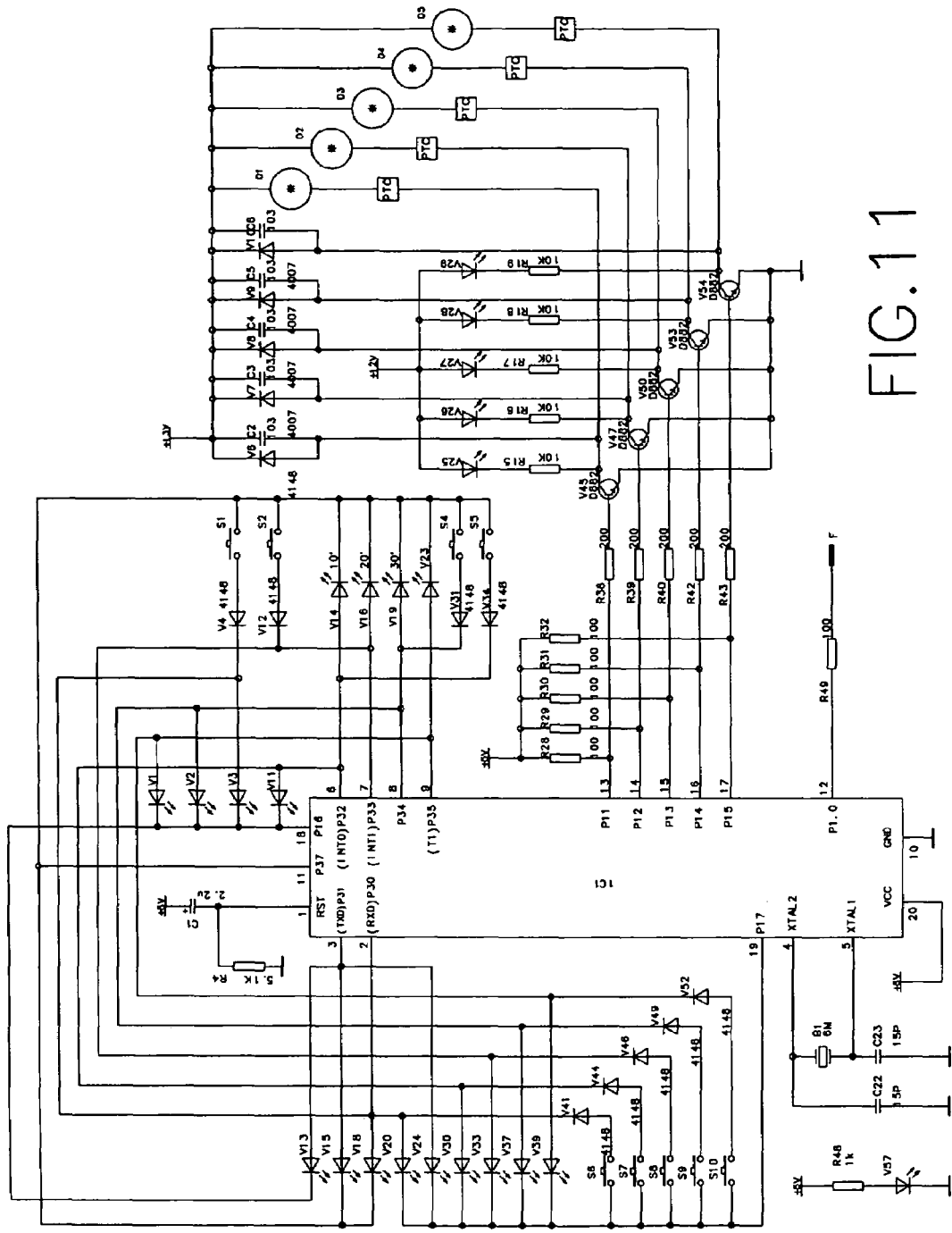
FIG. 11 is a circuit diagram of a massage controlling circuit of the air mattress according to the preferred embodiment of the present invention.

FIG. 11 shows a massage control circuit of the air mattress according to the present embodiment.

The massage process is controlled by the integrated circuit IC1. A push button switch S5, and triodes V34, V14, V11, V1 cooperatively form a switch circuit. A push button switch S4, triodes V31, and an output pin P34 of the integrated circuit IC1 cooperate to form a massage trigger circuit. Massage motors D1, D2, D3, D4 and D5 are controlled by pulses outputted from output pins P11, P12, P13, P14 and P15 of the integrated circuit IC1. Resistors R28, R29, R30, R31 and R32 are pull-up resistors. The massage motors D1, D2, D3, D4 and D5 are driven by resistors R36, R39, R40, R42, R43 and triodes V45, V47, V50, V53, V54, respectively. Diodes V25, V26, V27, V28, V29 and resistors R15, R16, R17, R18, R19 are state indicators and pull-up triggers, respectively. Diodes V6, V7, V8, V9, V10 and capacitors C2, C3, C4, C5, C6 cooperatively form a peak surge absorbing circuit. Overcurrent protectors for the massage motors D1, D2, D3, D4 and D5 are positive temperature coefficient devices (PTC). Selectable state indicators are indicted with V15, V18, V20, V24, V30, V33, V37 and V39. State select buttons are indicated with S6, S7, S8, S9 and S10, respectively. The push button switch S1, diodes V1, V2, V3, V4 and an output pin P1.6 cooperatively form a massage intensity select circuit. State select button S2, diodes V12, V14, V16, V19 and an output pin of P33 cooperatively form a timer select circuit.

Referring back to FIG. 5, the control center 111 comprises a refrigerator 308 and an integrated control chamber 303. A bracket is generally arranged in the refrigerator 308. A water reservoir pan sits at a bottom of the refrigerator 308. A plurality of operational buttons 304 and a display screen are generally arranged on an operation panel of the integrated control chamber 303. The integrated control chamber 303 can be operated manually or by a remote controller 112 (shown in FIG. 3). An air charging chamber 314, a cold source chamber 309, and a water tank chamber 310 are arranged at a rear portion of the control center 111.

The air charging chamber 314 comprises an air charger 302. The cold source chamber 309 includes a semiconductor thermo (cold or warm) energy generator 222 and a storage refrigerator 307 therein. The water tank chamber 310 includes the water tank 213 and the water pump 211 therein. The water tank 213 further comprises the electrical heater 214 and the water level monitor 218.

A massager wiring interface A, an air charging interface B for the air cushion 105, and an air charging tube interface C for the air bags 107 are arranged at a rear portion of the air charging chamber 314. An inlet interface E of the water tank 213 for communication with the water exhausting tube 208, an outlet interface E of the water tank 213 for communication with the water supplying tube 224, and a water inlet F of the water tank 213 are provided in a rear side wall of the water tank chamber 310.

The air charger 302, the operational buttons 304, the display screen, the water pump 211, the semiconductor thermo (cold or warm) energy generator 222, the electrical heater 214, the massager 505, and the water level monitor 218 are electrically connected to a control circuit in the integrated control chamber 303, respectively, and are operated by the operational buttons 304 or the remote controller 112. An exterior surface of the refrigerator 308 is preferably formed with a heat preservation layer for preventing energy losses.

Referring to FIG. 10, the air mattress comprises the air charger 302. The air charger 302 comprises an air generator and an air distributor. The air distributor comprises an air volume adjusting unit A for the air cushion 105, an air volume adjusting unit B for the massagers 501, and a controlling circuit board 727.

The air generator is generally a hermetic case, which comprises an internal case 709, an external case 707, a noise absorbing layer 708, and an air charging pump. The air charging pump is disposed in the internal case 709. The noise absorbing layer 708 is interposed between the internal case 709 and the external case 707. The noise absorbing layer 708 is generally made of a noise absorbing material. Alternatively, the noise absorbing layer 708 is a vacuum insulation layer. The internal case 709 and the external case 707 are securely attached to each other with rubber fixing posts 701. An air inlet 703 and an air outlet 712 are defined in the internal case 709 and the external case 707. The inlet 703 is composed of a plurality of apertures. The air charging pump comprises a magnetic oscillator 702, a magnet 704, a cylinder 705, a clamp 706 and a valve member 710. The structure of the air charging pump is well known to the ordinary skilled artisan, which will not be explained in detail hereinafter.

One end of an air transfer tube 713 communicates with the air outlet 712 of the air generator, and the other end thereof communicates respectively with an air volume adjusting unit A for the air cushion 105 and an air volume adjusting unit B for the air bags 107 via a three-way tube 714.

The air volume adjusting unit A is composed of an air supplying electromagnetic valve DZ1 for the air cushion 105, an air electromagnetic gate valve DZ0, an air exhausting electromagnetic valve DZ2 for the air cushion 105, a six-way tube 721 having a port 725 for connection with an air charging linkage tube 726, an air exhausting switch 722 for the air cushion 105, a soft-level pressure switch 723 for the air cushion 105, and a rigid-level pressure switch 724 for the air cushion 105. One end of the air supplying electromagnetic valve DZ1 is connected to a linkage tube 718. The other end thereof is connected to the air electromagnetic gate valve DZ0 that is in turn connected to a port of the six-way tube 712. The air exhausting electromagnetic valve DZ2, the air exhausting switch 722, the soft-level pressure switch 723, the rigid-level pressure switch 724, and the air charging linkage tube 726 are connected to the other ports of the six-way tube 721, respectively.

The air volume adjusting unit B is composed of an air supplying electromagnetic valve DZ3 for the air bags 107, an air exhausting electromagnetic valve DZ4 for the air bags 107, a five-way tube 728 having a port 731 for connection with an air charging linkage tube 732 for the air bags 107, an air exhausting switch 729 for the air bags 107, and an air charging switch 730 for the air bags 107. One end of the air supplying electromagnetic valve DZ3 is connected to the three-way tube 714. The other end thereof is connected to a port of the five-way tube 728. The air exhausting pressure switch 729 for the air bags 107, the air charging switch 730 for the air bags 107, and the air charging linkage tube 732 for the air bags 107 are connected to the other ports of the five-way tube 728, respectively. The air discharging switch 722 for the air cushion 105, the soft-level pressure switch 723 for the air cushion 105, the rigid-level pressure switch 724 for the air cushion 105, the air discharging switch 729 for the air bags 107, and the air charging switch 730 for the air bags 107 are electrically connected to a controlling circuit board 727. The controlling circuit board 727 includes an air charging control circuit (shown in FIG. 12), and a massage control circuit (shown in FIG. 11).

The air generator is activated to work upon execution of an instruction for charging the air. Firstly, a magnetic oscillator 702 generates a high frequent magnetic vibration that correspondingly causes a high frequent relative reciprocating movement between a permanent magnet 704 and a magnetic oscillator 702. A force generated by the movement is exerted on the cylinder 705 by means of a clamp 706 that is formed on the permanent magnet 704, thereby causing a high frequent repeated movement, i.e., compression, decompression, re-compression, and re-decompression, of the cylinder 705. Therefore the air is introduced into the air generator continuously through the air inlet 703. The air compressed in the air generator is forced out through an air outlet 712 and then introduced into the air volume adjusting unit A and the air volume adjusting unit B via an interface tube 711, the three-way tube 714, and a link tube 713 interconnected between the interface tube 711 and the three-way tube 714.

Operational principle of the air distributor is set forth below.

The air mattress of the present invention can be selectively operated at different rigid-soft levels by presetting and controlling the air pressure of the air mattress at corresponding different levels. For instance, in the present embodiment, the rigid-soft level of the air mattress is set as two levels, i.e., a rigid level and a soft level.

An operational principle of the air mattress operating at the rigid level is illustrated as follows: when filling air into the air mattress, the air generator and the air supplying electromagnetic valve DZ1 and the air electromagnetic gate valve DZ0 of the air cushion 105 are opened. The rigid-level pressure switch 724 for the air cushion 105 of the air volume adjusting unit A is opened. The air is introduced into the air cushion 105 via the six-way tube 725. Meanwhile, the air exhausting electromagnetic valve DZ2 of the air cushion 105 is closed. When the air pressure of the air cushion 105 reaches a predetermined pressure value, the air supplying electromagnetic valve DZ1 and the air electromagnetic gate valve DZ0 are closed and the air generator is shut down by means of the rigid-level pressure switch 724.

An operational principle of the air mattress operating at the soft level is illustrated as follows: when the soft level is selected, the air supplying electromagnetic valve DZ1 and the air electromagnetic gate valve DZ0 are opened. The soft-level pressure switch 723 is opened. The air is introduced into the air cushion 105 via the six-way tube 725. Meanwhile, the air outlet electromagnetic valve DZ2 for the air cushion 105 is closed. When the air pressure of the air cushion 105 reaches a predetermined pressure value, the air supplying electromagnetic valve DZ1 and the air electromagnetic gate valve DZ0 are closed and the air generator is shut down by means of the soft-level pressure switch 723.

When the air cushion 105 is operated in the soft state, in order to operate in the hard state, a rigid level instruction is required to be executed. Upon execution of the rigid level instruction, the air generator, the air supplying electromagnetic valve DZ1, the air electromagnetic gate valve DZ0, and the rigid-level pressure switch 724 are simultaneously opened. When the air pressure of the air cushion 105 reaches the predetermined rigid level pressure value, the air supplying electromagnetic valve DZ1, the air electromagnetic gate valve DZ0, and the rigid-level pressure switch 724 are shut down by means of the rigid-level pressure switch 724. Meanwhile, the air generator is shut down.

When the air cushion 105 is operated in rigid state, in order to operate in the soft state, a soft level instruction is required to be executed. Upon execution of the soft level instruction, the air exhausting electromagnetic valve DZ2 and the air exhausting switch 722 for the air cushion 105 are opened to exhaust the air. When the air pressure of the air cushion 105 reaches the predetermined soft level pressure value, the air exhausting electromagnetic valve DZ2 of the air cushion 105 and the air exhausting switch 722 are closed by means of the soft-level pressure switch 723.

In other words, the air supplying electromagnetic valve DZ1 is operatively communicating with the air chambers 113 to guide a predetermined volume of air thereinto and the air exhausting electromagnetic valve DZ2 is arranged to operatively discharge the air from said air chambers 113, such that when the air chambers 113 reached a predetermined air pressure, the air supplying electromagnetic valve DZ1 and the air exhausting electromagnetic valve DZ2 are closed to retain the air pressure in the air chambers 113 so as to adjust said rigid-soft level of the air cushion 105 for the air mattress.

An operational principle of an air volume adjusting system for the air bags 107 is illustrated as follows: the massager 501 starts to operate upon execution of a massage instruction. The air generator and the air supplying electromagnetic valve DZ3 are opened. The air is introduced into the air bags 107 via the air transfer tube 713, the air supplying electromagnetic valve DZ3, and the five-way tube 728. Meanwhile, the air supplying electromagnetic valve DZ1 for the air cushion 105 and the air volume adjusting unit A are both in a closed state.

When the air pressure of the air bags 107 reaches a predetermined pressure value, the air generator and the air supplying electromagnetic valve DZ3 are shut down by means of the air charging switch 730 for the air bags 107. When the massage operation is finished, the air outlet electromagnetic valve DZ4 is opened automatically to exhaust the air. When the air pressure of air bags 107 reaches a predetermined value, the air outlet electromagnetic valve DZ4 is shut down by means of the air exhausting switch 729 for the air bags 107.

Figure 12:
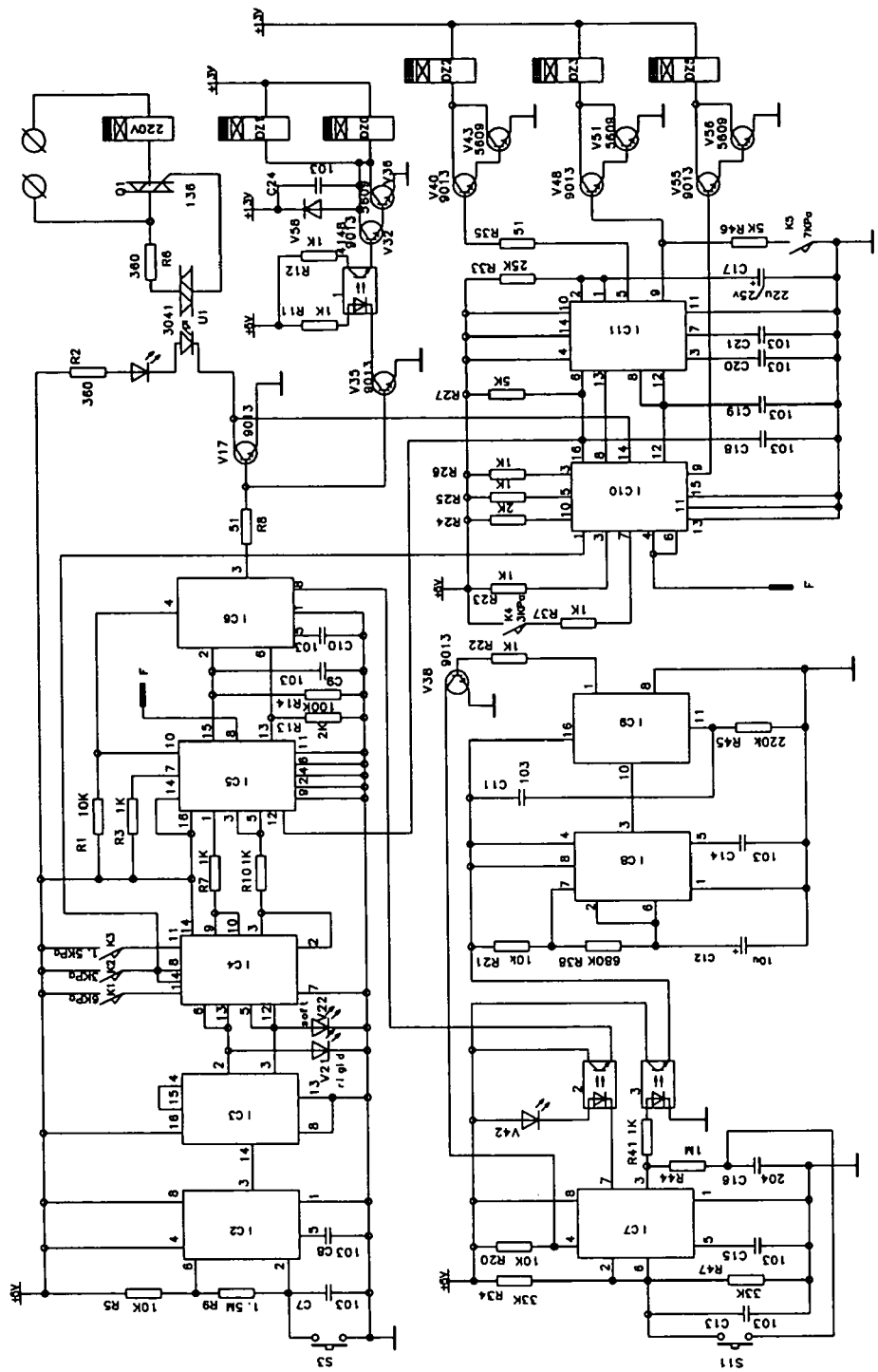
FIG. 12 is a circuit diagram of an air charging controlling circuit of the air mattress according to the preferred embodiment of the present invention.

FIG. 12 is a circuit diagram of an air charging control circuit of the air mattress according to the present embodiment. The air mattress of the present invention can achieve numerous adjusting functions by various designs of the control circuit such as follows:

1. Rigid-soft Adjustable Function of the Air Mattress

A rigid-soft degree of the air mattress of the present invention can be achieved by means of adjusting the air pressure of air mattresses to a corresponding value/level. For instance, in the present embodiment, the rigid-soft degree of the air mattress is preset as a rigid level and a soft level, i.e., to obtain a rigid mattress, a predetermined air pressure of the mattress is set as 6 Kpa; and to obtain a soft mattress, a predetermined air pressure of the mattress is set as 3 Kpa. The main control circuit is a loop comprised of a push button switch S3, integrated circuits IC2, IC3, IC4, IC10, IC11 and the air exhausting electromagnetic valve DZ2 for the air cushion 105. Rigid-soft indicating lights are indicated with reference numerals V21 and V22, respectively. When the push button switch S3 is on, the push button switch S3, the resistors R5 and R9, the capacitors C7 and C8, and the integrated circuit IC2 cooperatively form a pulse loop/circuit. Calculation result of the integrated circuit IC3 is outputted from a pin 2 thereof to pins 6 and 13 of the integrated circuits IC4. Meanwhile the indicator V21 is illuminated showing the mattress is in a rigid state. The integrated circuit IC4 is controlled by air pressure switches K1, K2 and K3. The integrated circuits IC4, IC5, IC6, IC10, IC11 and resistors R1, R3, R7, R10, R13, R14, R23, R27 and capacitors C9, C10, C17, C18, C20 cooperatively form a comparison trigger loop/circuit.

When the air mattress is changed from a rigid state into a soft state, a pulse is outputted from a pin 5 of the IC11, and is transmitted via the resistor R35, the triodes V40 and V43 in that order, to trigger the air exhausting electromagnetic valve DZ2 to discharge the air until the air pressure of the air cushion 105 reaches the soft level. An operation principle for changing the mattress from the soft state to the rigid state is generally the same to that of changing the mattress from the rigid state to the soft state, except that, the air charger is triggered by a comparison trigger signal resulted from the pin 3 of the IC6, via a resistor R8, a triode V17, an optoelectronic trigger tube U1, a resistor R6 and a bi-directional thyristor Q1, to fill air into the air cushion until an air pressure of the air cushion reaches the hard level.

It should be noted that inventive features of the present invention are not limited to the control circuit illustrated in the present embodiment. For instance, the control circuit can be designed to allow the air pressure of the air mattress to be operable at a plurality of different levels.

2. Adjusting Air Pressure of the Mattress During Massage Treatment

During massage treatment, the air mattress is discharged such that the contour of a user's body comes into fitting contact with the surface of the air mattress. In addition, the air bags 107 in the mattress are charged so as to raise the massager to a position that the massager devices 106 come into fitting contact with the body.

Referring to FIGS. 11 and 12, during the massage process, the air mattress is discharged by means of opening the air exhausting electromagnetic valve DZ2 which is in turn triggered by a pin 5 of the integrated IC11, the resistor R35 and the triodes V40, V43. When discharging, the air pressure of the mattress is controlled by the integrated circuit IC4, the air pressure switches K2 and K3. The air bags 107 are charged by opening the air supplying electromagnetic valve DZ3 which is in turn triggered by a pin 9 of the IC11 and triodes V48 and V51. An air pressure of the air bags 107 is controlled by a resistor R46 and an air pressure switch K5 of the integrated circuit IC11. An output pin P1.0 of the integrated circuit IC1 outputs a pulse to the pins 4 and 6 of the integrated circuit IC10 and the pin 8 of the integrated circuit IC5. Thereafter, a calculation result of the integrated circuits IC5, IC10 and IC11 is outputted from a pin 10 of the integrated circuit IC5 to a pin 4 of the integrated circuit IC6 to lock the integrated circuit IC6 thereby making the air mattress become non-chargeable any more. After the massage process, the air bags 107 are discharged by means of opening the air outlet electromagnetic valve DZ4 which is triggered by a pin 9 of the IC10 and triodes V55, V56. Meanwhile, the integrated circuit IC6 is unlocked, accordingly. The air mattress is triggered to be charged by opening the air generator and the opens the air generator and the air supplying electromagnetic valve DZ1 which is in turn triggered by a pulse outputted from a pin 3 of the integrated circuit IC6 until the air pressure reaches a desired soft or rigid level.

3. Air Pressure Preservation of the Air Mattress

In the present embodiment, the soft level is preset in the range from 1.5 Kpa to 3 Kpa, and the rigid level is preset in the range from 3 Kpa to 6 Kpa. With the reference to FIG. 12, the integrated circuits IC4, IC5, IC6 and pressure signal switches K1, K2, K3 cooperatively form a decision circuit for determining whether an air pressure is at the soft or rigid level. If the air pressure is lower than 1.5 Kpa, or the air pressure is higher than 3 Kpa, an output pulse will be outputted from a pin 3 of the integrated circuit IC6 to drive the air charger to fill air into the air mattress. A resistor R51, a triode V17, a resistor R2, an air charging indicator U1, a resistor R6, and the bi-directional thyristor Q1 cooperatively form a control circuit for controlling the air generator. A triode V35, a resistor R11, the optoelectronic coupler G1, a resistor R12, triodes V32, V36 cooperate to form a switch controlling circuit for the air supplying electromagnetic valve DZ1 and the air electromagnetic gate valve DZ0.

4. Delay-to-charge Function of the Air Mattress

The air mattress according to the present embodiment can achieve a delay-to-charge function by means of a corresponding control circuit. For instance, a delay time is preset as 10 hours. Wherein a push button switch S11, a capacitor C13, resistors R47, R34, and R20, capacitors C15 and C16, resistors R44 and R41, a triode V42, optoelectronic couplers G2 and G3, and the integrated circuit IC7 cooperatively form a bistable pulse triggered and control circuit. Resistors R21 and R38, capacitors C12 and C14, and the integrated circuit IC8 cooperate to form an unstable oscillator pulse output circuit. A capacitor C11, resistors R45 and R22, and a triode V38 cooperatively form a binary pulse counting circuit.

When the push button switch S11 is on, a pin 3 of the integrated circuit IC7 outputs a high voltage and locks it. The integrated circuits IC8 and IC9 are actuated and powered by the optoelectronic coupler G3. Meanwhile, a pulse is outputted from a pin 7 of the integrated circuit IC7 so as to make the integrated circuit IC6 output a pulse from a pin 3 thereof regardless of being in any state. After a delay period of 10 hours, the integrated circuit IC7 is reset by a pulse outputted from a pin 1 of the integrated circuit IC9 via a resistor R22 and a triode V38.

Figure 16:
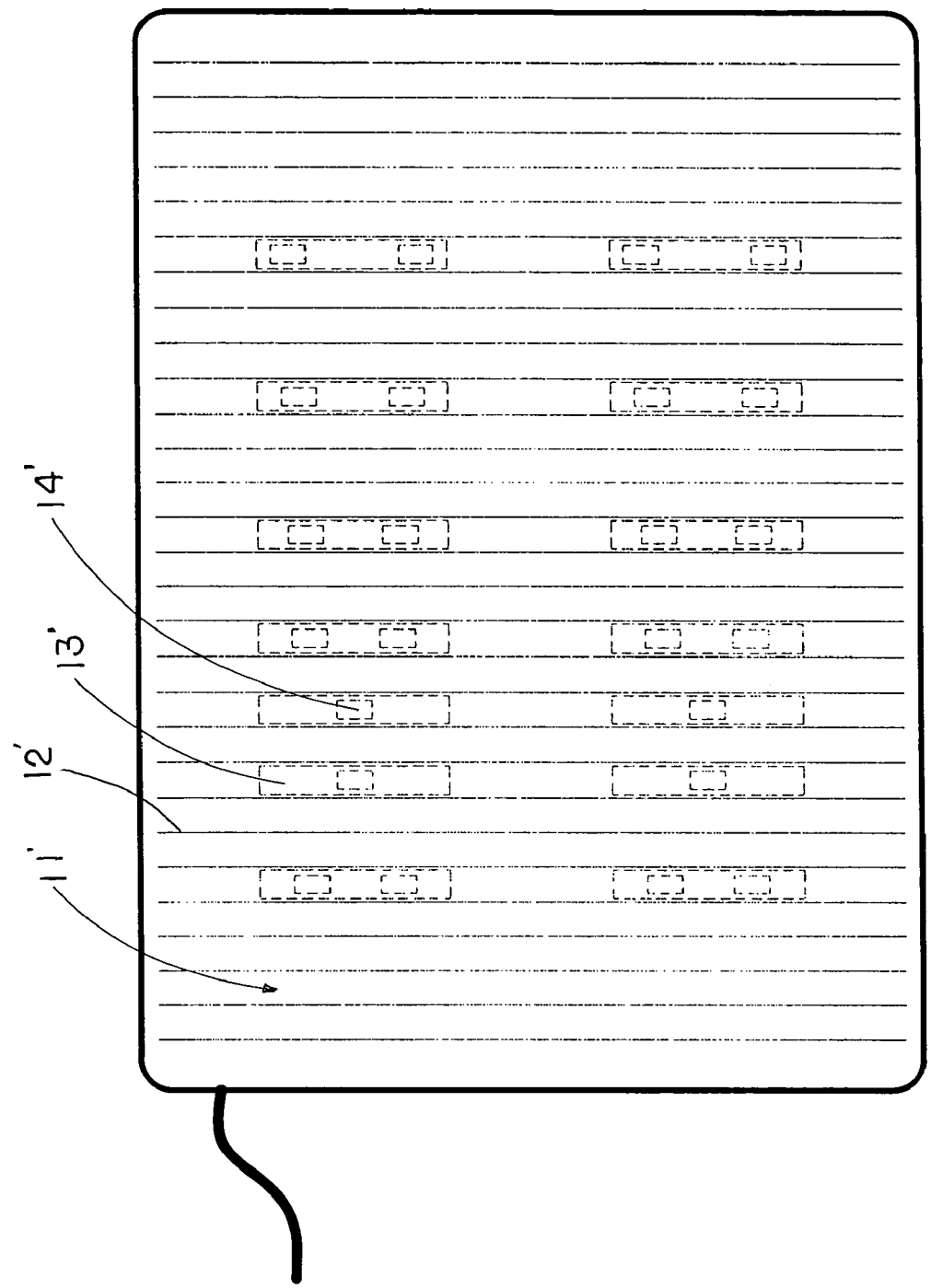
FIG. 16 is a schematic view of the alternative massaging arrangement of the mattress according to the above preferred embodiment of the present invention showing the massagers are ergonomically provided predetermined portions of the air mattress for massaging a loaded human body thereon.

FIGS. 13 to 17 illustrate an alternative mode of the massage arrangement of the air mattress. The air mattress comprises an air envelope 10' having s functioning port 20' and a plurality of partition walls 12' transversely extended therein to form a plurality of individual air chambers 11' communicating with the functioning port 20. Accordingly, the air chambers 11' are transversely extended along the air mattress. For example, when the air mattress has a length of 1.9 meter, there are twenty-nine partition walls 12' spacedly and transversely extended along the air envelope 10' to define thirty individual air chambers 11', so as to form a flat supporting surface (i.e. the outer layer) on the air envelope 10' for the user supporting thereon. The massage arrangement comprises a plurality of massage units selectively disposed in the air chambers 11' respectively for providing massage function at desired points on the user when the user rests on the air envelope 10'. As the above example, there are seven massage units supported within seven of the air chambers 11' for purposely and correspondingly matching with different locations of the user, such as one for shoulder portion, two for back, one for waist, one for butt, one for upper thigh, and one for lower calf as shown in FIG. 16.

Figure 13:
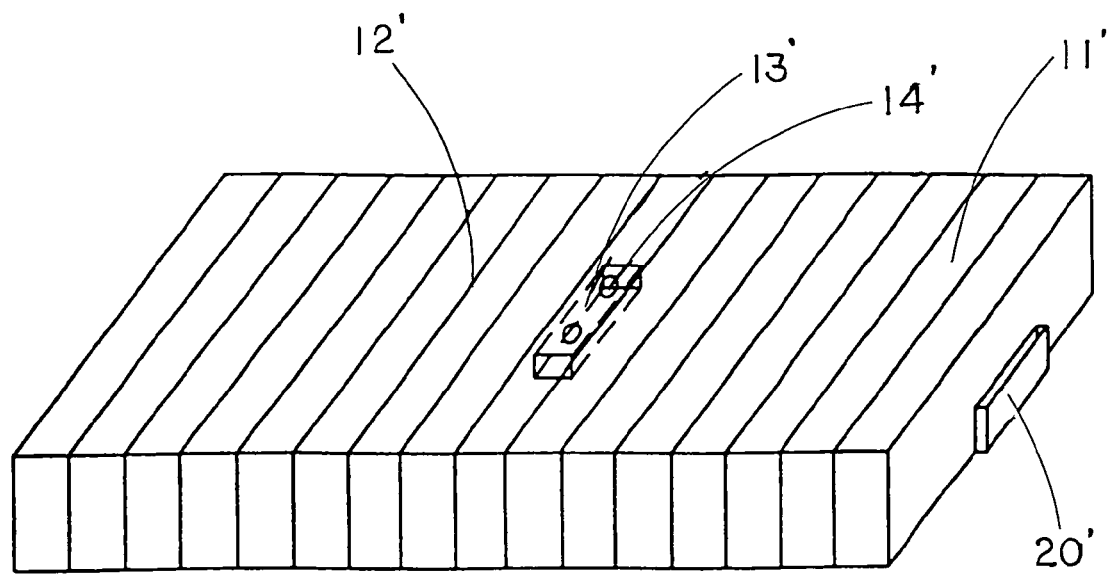
FIG. 13 illustrates an alternative mode of the massaging arrangement of the air mattress according to the above preferred embodiment of the present invention.
Figure 14:
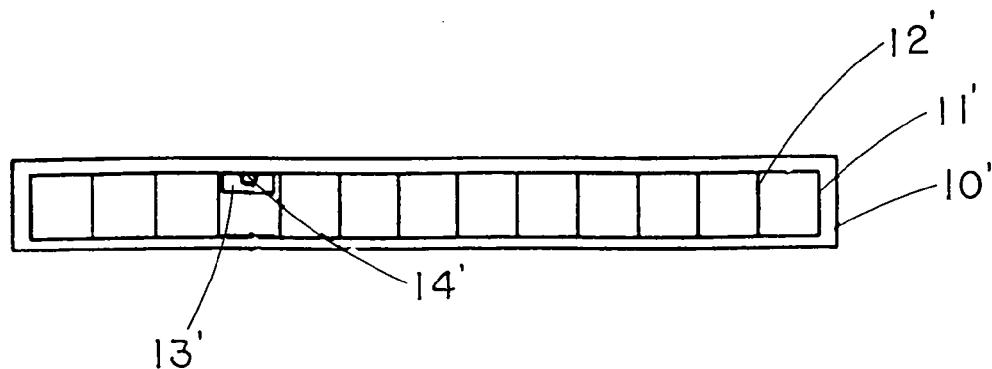
FIG. 14 is a schematic view of the alternative massaging arrangement of the air mattress according to the above preferred embodiment of the present invention.
Figure 15:
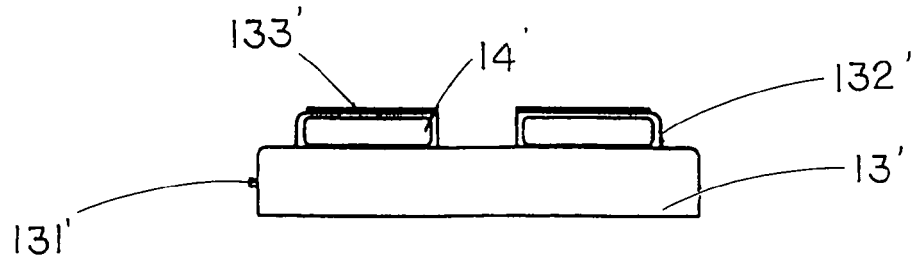
FIG. 15 is a sectional view of the alternative massaging arrangement of the air mattress according to the above preferred embodiment of the present invention.

As shown in FIG. 13, each of the massage units comprises an air bag 13' having an air passage 131' communicating with the functioning port 20', a massager bag 132' provided on the air bag 13', and a massager 14' received in the massager bag 132'. It is worth to mention that each of the massager bags 132' is adapted to hold two massagers 14' therein. Accordingly, the massager bag 132' has an inner cushioning layer encircling the massager 14'. Each of the massage units is substantially mounted at a ceiling of the respective air chamber 11' by mounting the massager bag 132' to the ceiling of the air chamber 11' via hook and loop fasteners so as to retain the massager 14' at a position underneath the supporting surface of the mattress envelope 10'.

Each of the massagers 14' is driven by an eccentric wheel motor as mentioned above for generating a massaging force towards the supporting surface of the mattress envelope 10'.

The massagers 14' are electrically connected to a power source via electrical wires.

Figure 17A:
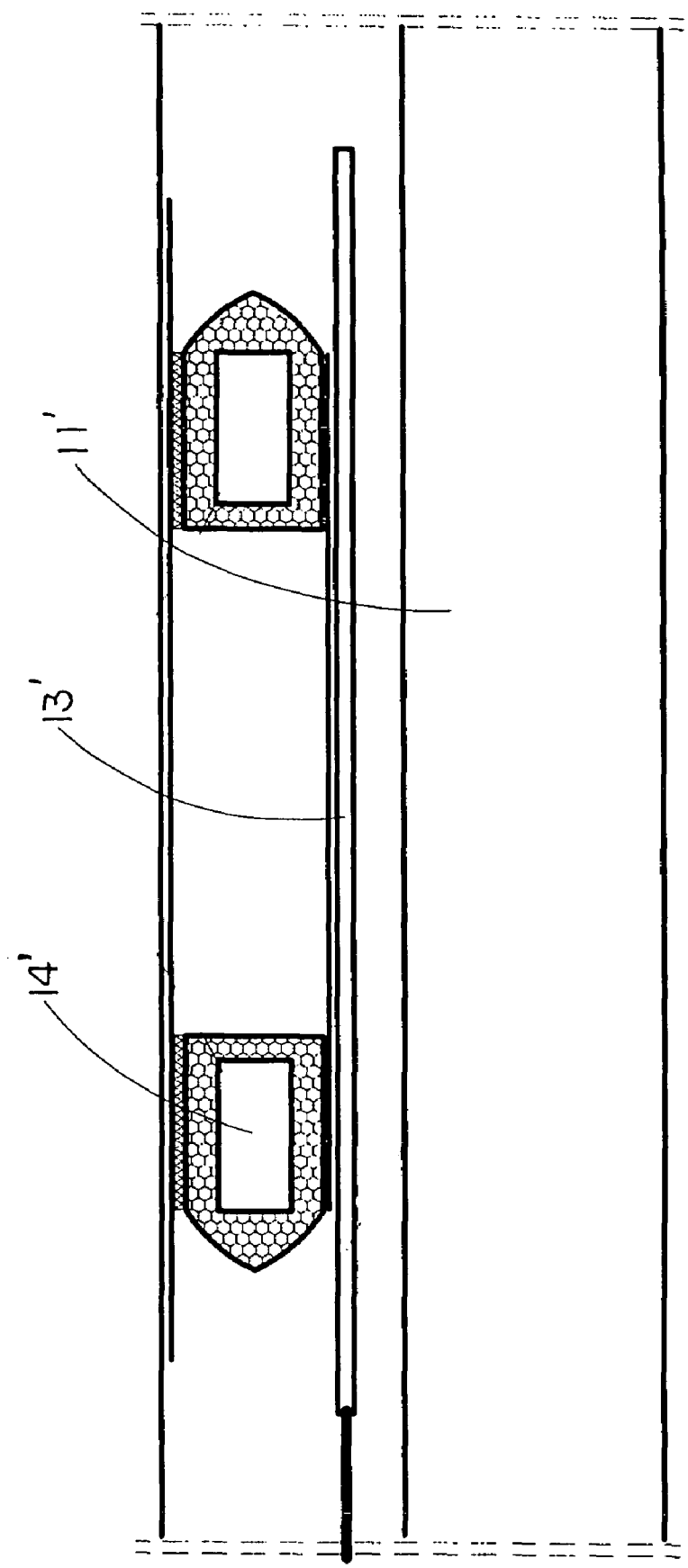
FIG. 17A is a schematic view of the alternative massaging arrangement of the mattress according to the above preferred embodiment of the present invention illustrating a pair of massagers received in the air bag with a stand-by manner.
Figure 17B:
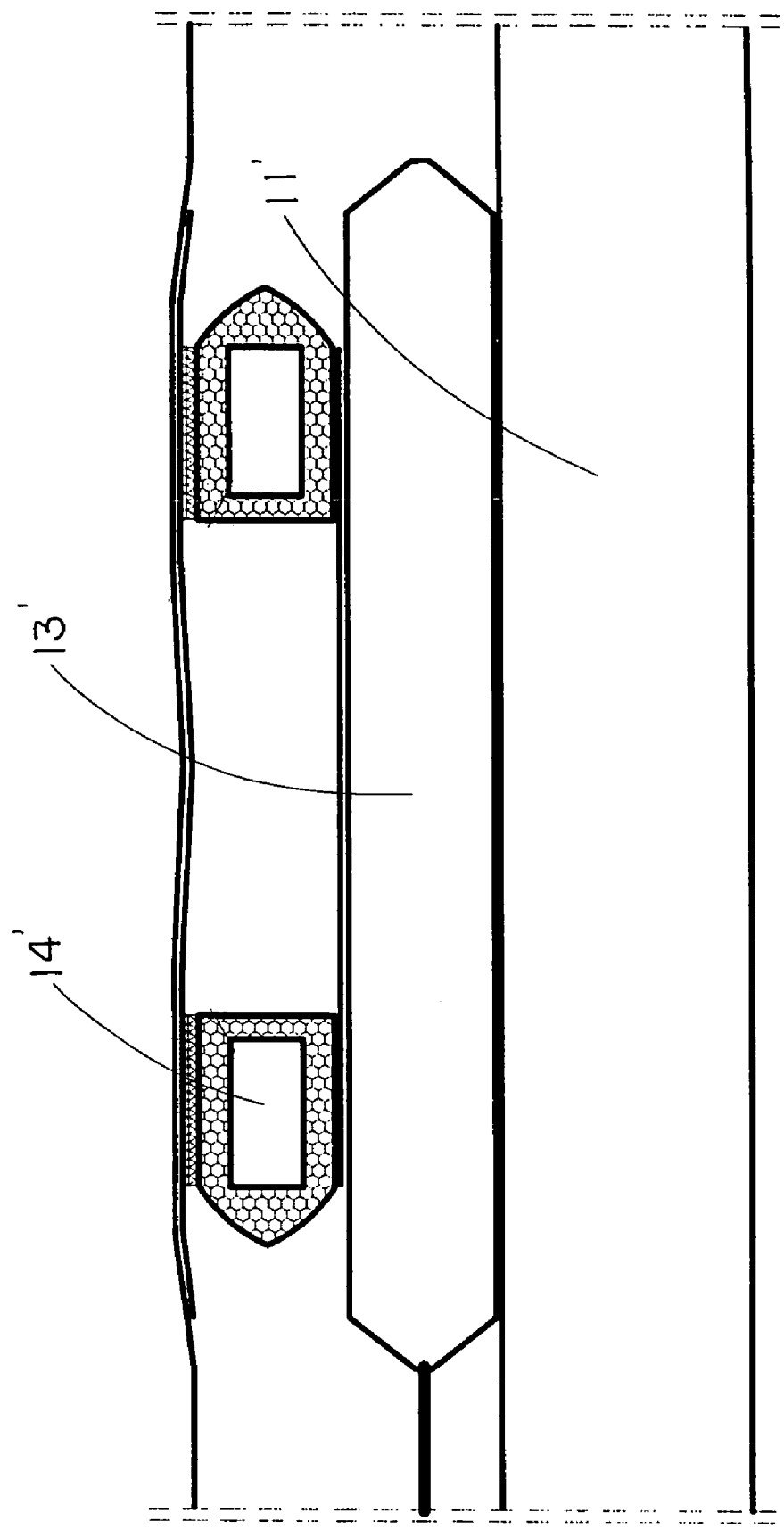
FIG. 17B is a schematic view of the alternative massaging arrangement of the mattress according to the above preferred embodiment of the present invention illustrating the massager bag is charged with pressurized air to upwardly urge the massagers for massaging purposes.

Accordingly, when the air chamber 11' is inflated to retain a predetermined air pressure therein, the air pressure inside the deflated air bag 13' is relatively smaller than the air pressure within the air chamber 11' as shown in FIG. 17A. Therefore, when the user rests on the supporting surface of the mattress envelope 10', he or she does not feel the massagers 14' under the supporting surface of the mattress envelope 10'. When the air bag 13' is inflated through the air passage 131' to retain a predetermined air pressure, the air pressure within the air bag 13' will push the massager 14 upwardly towards the supporting surface of the mattress envelope 10' so as to form a massage point thereon as shown in FIG. 17B. Therefore, when the user rests on the supporting surface of the mattress envelope 10', the massagers 14 will substantially contact with the user's body at the massage points. At the same time, the air pressure within the air chamber 11' is substantially reduced to maintain the air pressure within the air chamber 11' at a desired level to support the user. It is worth to mention that the air bag 13' is stopped to be inflated when the air bag 13' reaches the optimum air pressure via a control valve. The massager 14' is controllably operated to generate the massaging force according to desired massage mode, massage intensity, and/or massage duration upon execution of massage instruction set by the user.

During the operation of the massager 14', the air bag 13' is controlled by the air generator to retain the air pressure within the air bag 13' at a predetermined level. Once the massager 14' is switched off, the air pressure within the air bag 13' is released by opening an exhausting valve of the air generator such that the air bag 13' is deflated to return to its original condition. It is worth to mention that the air pressure within the air chamber 11' is correspondingly increased to maintain the air pressure at the desired level when the air bag 13' is deflated. It is worth to mention that the air generator is communicatively connected to the functioning port 20' to control the air pressures of the air chambers 11' and the air bags 13'.

In other exemplary embodiment, the air mattress can be configured as a twin size bed or even a king size bed. In case the air mattress is applied to a king size bed, two sets of massagers 14' can be provided within the mattress envelope 10'. Accordingly, a length of the mattress envelop 10' can be 2.2 meter that thirty-two partition walls 12' are spacedly and transversely extended along the air envelope 10' to define thirty-three individual air chambers 11', so as to form a flat supporting surface on the air envelope 10' for the user supporting thereon. Furthermore, there are seven individual air bags 13' selectively supported the air chambers 11' wherein each air bag 13' holds two massagers 14' therein for generating a massaging force to massage the user's body at different locations such as shoulder portion, back portion, waist portion, butt portion, upper thigh portion, and lower calf portion.

From what has been discussed above, the advantages of the air-filled mattress according to the present embodiment are mainly concluded, as follows:

1. A temperature of the air mattress can be desirably adjusted according to the ambient temperature.
2. The air mattress is capable of performing a massage treatment on a user by means of the massagers.
3. The air mattress is capable of performing health care function on the user by means of the far infrared emission.
4. The rigid-soft level of the air mattress is desirably adjustable according to requirements.
5. The air mattress can be operated in a manual manner or in a remote control manner according to requirements.
6. The air mattress can integrate all the abovementioned functions, or a certain individual function, or some of functions according to requirements.

Although the present invention has been described with reference to a specific embodiment, it should be noted that the described embodiment is not necessarily exclusive and that various changes and modifications may be made to the described embodiment without departing from the scope of the invention as defined by the appended claims.

What is claimed is:

1. An air mattress, comprising:
a mattress envelope having a compartment and comprising a thermal functional layer and an outer layer overlapped thereon;
an air cushion, which is received in said mattress envelope, comprising a plurality of individual air chambers evenly disposed in said compartment of said mattress envelope and an air supplying tube communicatively interconnecting said air chambers with each other;
a thermal control arrangement, which comprises:
a liquid supplying tube spirally extending at said thermal functional layer of said mattress envelope for guiding a flow of thermal liquid; and
a thermal energy generator arranged to regulate a temperature of said thermal liquid such that when said thermal liquid passes through said liquid supplying tube, said thermal liquid thermo-communicating with said thermal functional layer of said mattress envelope towards said outer layer so as to regulate a temperature of said mattress envelope; and
a massaging arrangement for providing a massaging function of said air mattress, wherein said massage arrangement comprises a plurality of massaging units selectively disposed in said air chambers respectively, wherein each of said massaging units comprises an air bag supported in said respective air chambers to communicate with said air supplying tube and a massager which is supported on said air bag and is arranged in such a manner that when said air bag is pumped in an inflated manner, said respective massager is pushed upward for generating a massaging force towards said outer layer of said mattress envelope,
wherein each of said massaging units further comprises a suspension bag suspendedly supported in said respective air chamber to receive said air bag and said massager in said suspension bag, such that said respective massager suspendedly supported in said air chamber at a position that said massager is mounted underneath said outer layer of said mattress envelope so as to transfer said massaging force towards said outer layer of said mattress envelope.

2. An air mattress, comprising:
a mattress envelope having a compartment and comprising an outer layer;
an air cushion, which is received in said mattress envelope, comprising a plurality of individual air chambers evenly disposed in said compartment of said mattress envelope and an air supplying tube communicatively interconnecting said air chambers with each other; and
a massaging arrangement for providing a massaging function of said air mattress, wherein said massage arrangement comprises a plurality of massaging units selectively disposed in said air chambers respectively, wherein each of said massaging units comprises an air bag supported in said respective air chambers to communicate with said air supplying tube and a massager which is supported on said air bag and is arranged in such a manner that when said air bag is pumped in an inflated manner, said respective massager is pushed upward for generating a massaging force towards said outer layer of said mattress envelope,
wherein each of said massaging units further comprises a suspension bag suspendedly supported in said respective air chamber to receive said air bag and said massager in said suspension bag, such that said respective massager suspendedly supported in said air chamber at a position that said massager is mounted underneath said outer layer of said mattress envelope so as to transfer said massaging force towards said outer layer of said mattress envelope.

3. The air mattress, as recited in claim 2, wherein said massaging arrangement further comprises draught bands connecting said suspension bags with each other.

4. The air mattress, as recited in claim 2, wherein each of massaging units further comprises a massager bag provided on said air bag to receive said massager in said massager bag such that when said air bag is inflated, said massager is pushed upwardly towards said outer layer of said air envelope as a massaging point thereon.

5. The air mattress, as recited in claim 4, wherein said respective air chamber is deflated when said corresponding air bag therein is inflated to retain a predetermined air pressure within said air chamber.

6. The air mattress, as recited in claim 5, wherein each of said massager bags is mounted at a ceiling of said respective air chamber via hook and loop fasteners to retain said respective massager at a position underneath said outer layer of said mattress envelope.

* * * * *